United States Patent [19]
Birnbaum et al.

[11] Patent Number: 5,627,643
[45] Date of Patent: May 6, 1997

[54] METHOD AND DETECTOR FOR SEPARATION PROCESSES

[76] Inventors: Staffan Birnbaum, Gråsparvsvaägen 74 S-227 31; Jonas Johansson, Tellusgatan 6 C, S-224 57; Per-Olof Larsson, Fågelhundsvägen 56, S-226 53, all of Lund; Akiyoshi Miyabayashi, Regementsgatan 68 B, S-217 51, Malmö ; Klaus Mosbach, Lackalänga 31-38, S-244 94, Furulund; Staffan Nilsson, Siriusgatan 14, S-224 57, Lund; Sune Svanberg, östgötavaägen 12, S-222 25, Lund; Karl-Gustav Wahlund, Sångarevägen 6 E, S-224 71, Lund, all of Sweden

[21] Appl. No.: 313,319
[22] PCT Filed: Apr. 7, 1993
[86] PCT No.: PCT/SE93/00305
 § 371 Date: Oct. 7, 1994
 § 102(e) Date: Oct. 7, 1994
[87] PCT Pub. No.: WO93/20435
 PCT Pub. Date: Oct. 14, 1993

[30] Foreign Application Priority Data

Apr. 7, 1992 [SE] Sweden .................................. 9201089

[51] Int. Cl.⁶ .................................................. G01N 27/26
[52] U.S. Cl. .......................... 356/344; 204/452; 204/603; 73/61.58; 210/656; 210/85; 210/198.2
[58] Field of Search ....................... 356/344; 204/299 R, 204/180.1, 182.8

[56] References Cited

U.S. PATENT DOCUMENTS 3,623,812 11/1971 Hannig ..................... 356/344
4,420,383 12/1983 Fujiwara et al. .................. 356/344
4,666,578 5/1987 Yamamoto .
4,786,813 11/1988 Svanberg et al. .
5,006,210 4/1991 Yueng et al. .................. 204/299 R
5,061,067 10/1991 Yamamoto et al. ................. 356/344
5,098,536 3/1992 Anderson .................. 356/344
5,141,609 8/1992 Sweedler et al. .................. 356/344
5,162,654 11/1992 Kostichka et al. .................. 356/344
5,290,419 3/1994 Kambara et al. .................. 356/344

FOREIGN PATENT DOCUMENTS 0214713 3/1987 European Pat. Off. .
3438799 10/1983 Germany ................. 356/344
3812899 10/1989 Germany .
3606231 10/1991 Germany .
5052810 3/1993 Japan ................. 204/299 R

OTHER PUBLICATIONS

"Disc Electrophoresis" Canal Industrial Co. Oct. 1964.
Carchon et al, International Chromatography Laboratory, vol. 6, pp. 17–22 (Sep./1991).
Goodall et al, LC-GC, vol. 8, No. 10, pp. 788–799 (1990).
International Publication WO 89/10550, 2 Nov. 1989.

Primary Examiner—Hoa Q. Pham
Attorney, Agent, or Firm—Birch, Stewart, Kolasch & Birch, LLP

[57] ABSTRACT

The present invention comprises a method Of detecting and quantifying components separated by capillary electrophoresis or other techniques using thin capillaries in the separation. The method of the present invention comprises irradiating the whole or large parts of the capillary at short time intervals and detecting the fluorescence originating from the sample components, preferably by a CCD detector (charge coupled device). Thereby, an instantaneous image of the progress of the separation process is obtained. The present invention further comprises an apparatus for performing this detection.

20 Claims, 3 Drawing Sheets

METHOD AND DETECTOR FOR SEPARATION PROCESSES

In the bioscientific field there is a great need of being capable of analysing complex mixtures of biomolecules. Examples are the analysis of metabolites, proteins, antibodies and drugs in clinical analysis. Another example is the analysis of protein composition in the fermentation of proteins specified by genetic engineering.

A usual way of performing bioanalyses is to separate a sample into its constituents and then quantify the constituents. Conventional separation methods are chromatography and electrophoresis. Electrophoresis has a strong position just for analysis. The reason is that the method is high-resolving, which among other things means that many components can be analysed in one and the same run. In combination with suitable detection methods for the separated substances, the method may also be made very sensitive. On the other hand, the method is generally slow, typical separation times being in the range of 1–10 hours.

For the last couple of years a special form of electrophoresis has attracted much attention, viz. capillary electrophoresis. The electrophoretic process takes place in thin capillaries of quartz (inside diameter about 0.005–0.1 mm). The thin capillaries make it easy to cool off the Joule heat that is generated during the process of the electrophoresis. It is therefore possible to use very high field intensities in the electrophoretic separation, e.g. 300 V/cm. Since the high field strength gives a very rapid migration rate, the separation times become favourably short with capillary electrophoresis. In normal electrophoresis, temperature gradients easily arise in the separation bed. Temperature gradients lead to a heavily impaired resolution of the sample components. This problem is eliminated by the capillary electrophoresis technique, where the thin capillaries are easy to cool and therefore do not lead to problematic temperature gradients. Consequently, also the resolving power is very good with capillary electrophoresis. An illustrative review article has been written by H. Carchon and E. Eggermont (International Chromatography Laboratory, Vol. 6, pages 17–22, 1991).

The detection and quantification of mixtures separated by capillary electrophoresis are usually performed with a UV/Vis detector or fluorescence detector (a review of different detection principles for capillary electrophoresis has been written by D. M. Goodall, D. K. Lloyd and S. J. Williams in LC-GC, Vol. 8, No. 10, 1990, pages 788–799). These detectors are always placed at one end of the capillary. Usually a light beam is made to pass perpendicularly through the capillary, and a detector measures the amount of light that has passed or the amount of fluorescence that has been induced. The separated substances are thereby detected one after the other as they pass the detector. This means that the electrophoresis must continue until all the substances have passed the detector. Often the number of substances in the sample is not known, and the electrophoretic run must therefore proceed considerably longer than actually necessary in order to ensure that all the sample components have really passed the detector. A limiting factor of capillary electrophoresis is thus seen here, viz. the serial detection principle, i.e. the sample components being detected one after the other. If instead a detection principle is provided where the whole capillary is examined momentarily by a special detector, a parallel detention principle is obtained where all the components are detected simultaneously. The present invention discloses just such a principle and the construction of suitable apparatus.

With the present invention, a sample may be separated into components in a thin capillary. At short intervals during the separation, the whole, or at least a large part, of the capillary may be simultaneously irradiated and either the emitted or absorbed light may be detected, thus creating successive momentary images of the separation pattern. The detection of the light may be based on, but is not limited to, fluorescence and light scattering of the sample components.

The novel detection principle resides in monitoring the capillary electrophoresis by a detector which at short intervals examines the whole capillary and registers where the sample components are in the capillary. Simultaneously, the detector registers spectral characteristics of the sample components, which facilitates their identification. The data obtained are stored in a computer.

SUMMARY OF THE INVENTION

To explain the manner of function the following short apparatus description will give guidance (a more detailed description will be given further on): The detector according to the present invention consists of a strong light source, e.g. a laser. The laser irradiates the whole capillary, preferably at short time intervals. Upon each irradiation the spatially separated sample substances will fluoresce. The fluorescence emission from the capillary is focused via a lens system onto a CCD detector (charge coupled device), generating an electronic image of the appearance of the capillary. A computer stores this image. Between each irradiation time, the sample components move a little, this movement being registered by the CCD detector. The computer continuously transforms the stored data and can in real-time present the progress of the separation on a display screen. This is a very great advantage. It may be seen directly on the computer screen when the separation of the sample components is sufficiently good for them to be quantified with sufficient precision. Optionally the computer may perform this judgement by itself. This means great savings of time, since the separation may be stopped much earlier than in the case of a detector placed at the end of the capillary. This is particularly the case if the sample contains very slowly migrating components.

With the present invention it is possible to reverse the polarity of the electrophoretic process when a sufficiently good separation has been obtained and wash out the sample backwards to prepare the capillary for the next sample. If the sample contains slowly migrating substances, it is easily understood that the invention leads to an improvement in efficiency (sample/hour) by a factor of 10.

Another advantage of the novel detector is that the operator/computer has a superior control of the separation process. All separation processes with serial detection, including normal capillary electrophoresis, suffers from the problem that one cannot be sure that all components have actually reached the detector when the separation is stopped. This problem is effectively solved by monitoring the whole separation capillary in accordance with the invention.

Fields which may particularly take advantage of the novel detector may be envisaged. One of them is sequence analysis of genes, where analytical speed combined with reliable determination is very important. The sample, which has been generated via Sanger's method with controlled interrupted replication, consists here of a mixture of oligonucleotides of different lengths. The oligonucleotides are labelled with fluorescent dyes, e.g. Rhodamine 110, Rhodamine 6G, Tetramethyl Rhodamine and X-Rhodamine, which are well adapted to excitation by an argon laser (514 nm). Very rapid separation cycles are possible here. As soon as a sufficient separation has been obtained, the system may be regenerated through pole reversal. Also much longer sequences than are normally practical to work with will thereby be possible to handle.

Another very interesting field is the study of protein-ligand interactions. If the protein has a higher migration rate than the ligand, the ligand is first applied to the capillary. A while later the protein is applied. The protein will now migrate into the slowly migrating segment with ligand, and after still some time it will have passed the ligand segment completely. In connection with the passage, interactions take place which will be reflected in the migration rates of the components. The novel detector makes it possible to follow these interactions very accurately. By afterwards analysing the fronts arisen and their composition, very interesting information may be extracted concerning equilibrium constants and kinetic rate constants.

DETAILED DESCRIPTION OF THE INVENTION

The above description of the invention relates to capillary electrophoresis. The same principal advantages apply to electrokinetic chromatography, i.e. separation with capillary electrophoresis equipment where the actual separation process, however, is not electrophoretic but chromatographic. Also separations by HPLC technique in thin glass or silica columns may make use of the novel detection method.

There are a number of alternative embodiments of the invention, including various ways of connecting the light source (laser or other light source) to the capillary. One way is to irradiate the fiber perpendicularly to its longitudinal direction. Another way is to inject the exciting light through the end surface of the capillary. This way may be expected to give a particularly even and effective irradiation simultaneously as the amount of stray light is minimized. A number of laser types may be used as the excitation source, the choice being determined inter alia by the desired excitation wavelength. A HeCd-laser (e.g. of Liconix make) will give suitable lines at 442 and 325 nm. A small argon ion laser (e.g. of Spectra Physics make) will give blue-green lines, but also UV-light may be obtained around 350 nm. A pulsated nitrogen laser (e.g. of Laser Science Inc. make) emits at 337 nm and may also be used to pump a dye laser for generating arbitrary visible wavelengths.

The total fluorescence may without wavelength discrimination be imaged onto a linear detector (diode row) after the exciting laser light has been suppressed by means of a sharp high-pass filter, suitably a colour filter (e.g. of Schott make). Suitable diode rows for the purpose are marketed by e.g. EG&G or Reticon. The diode row has often a length of 25 mm and 1024 individual diodes, but is also available in longer designs. The lens system is selected such that the straight capillary is imaged with correct reduction onto the diode row in such a way that each diode corresponds to a certain position along the capillary. The spatially resolved detector signal may be read to a computer via a control unit. If a pulsated excitation source is used (e.g. a nitrogen laser), a gated microchannel plate may be used before the diode row for effective amplification of the fluorescent light, simultaneously as a suppression of the background light is obtained.

The detector system will be particularly powerful if, simultaneously as the spatially resolved signals are registered, also the spectral colour distribution of the fluorescent light may be obtained. This may be done by imaging the capillary on the entrance slit of a spectrometer. The slit is arranged in parallel with the grooves of the grating, which spectrally separates the light perpendicularly to the slit direction. In a focal plane the light falls onto a two-dimensional CCD detector, where one dimension corresponds to different positions along the capillary and corresponding spectra are in the other dimension. Via a reading unit spectra may be read for the different positions. Spectrometers arranged in such a way (imaging Spectrometers) are known from satellite-borne remote analysis sensors. A computer may evaluate spectra and compare them with stored reference spectra for a refined analysis. Alternatively, the intensity in given wavelength ranges may be read corresponding to the emission bands of fluorescent labels having a known emission.

A limited spectral analysis may also be obtained by utilising a linear detector (diode row) if the fluorescent light by means of a special mirror system is first divided into e.g. four parts which are individually focused to image lines. By correct positioning, of the mirrors these image lines may be placed in a row after each other along the linear detector. Into the four separated beam paths other means such as, band-pass filters are introduced which isolate the fluorescence light, for example from fluorescent labels used in DNA sequencing. In this manner spatially resolved images may simultaneously be obtained from which the positions of the different labels along the capillary may be seen. The beam division and registering method for fluorescence is performed here by a technique disclosed in the Swedish patent No. 455646 (Fluorescence imaging system).

As mentioned above, the signals may be read and analysed when a suitable separation between the components has been obtained. Since the components migrate individually at a uniform rate, the information along the capillary may, however, be read at several times during a long time interval and be co-calculated in the computer to signals exhibiting a combination of favourable signal strength and resolution properties. In this way an optimised function as regards speed and resolution may be obtained for an instrument based on the principles given in the present invention.

BRIEF DESCRIPTION OF THE DRAWINGS

FIG. 1 shows an experimental set-up with a diode row as detector. A laser-light source with associated optics (1) irradiates the capillary electrophoretic capillary (2). Substances (3) present in the capillary (2) will then fluoresce. The fluorescent light is focused by a lens system (4) onto a diode row (5). The signal from the diode row is sent to a computer (6) which on its display screen can show the positions of the separated substances (3) in real-time.

FIG. 2 shows an experimental set-up with a cooled CCD camera as detector. A power unit (1) applies a voltage over a capillary (2) in which separation of the sample components takes place. A laser light source (3) irradiates the capillary (2) via a modulating lens system (4). The fluorescent light from fluorescing sample components in the capillary (2)

Figure 1:
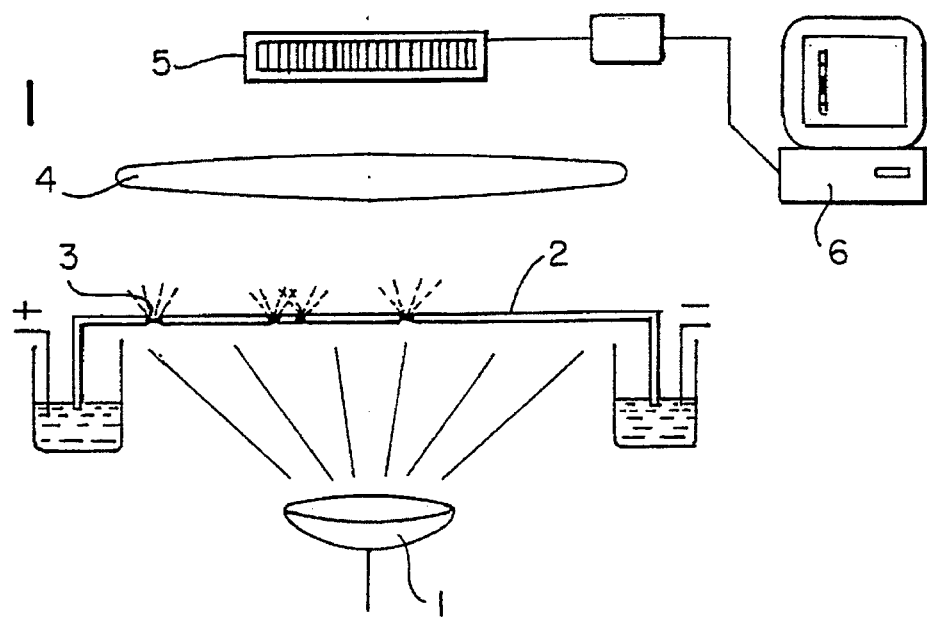
FIG. 1. Experimental set-up for separation and analysis of spectral properties-of sample components.
Figure 2:
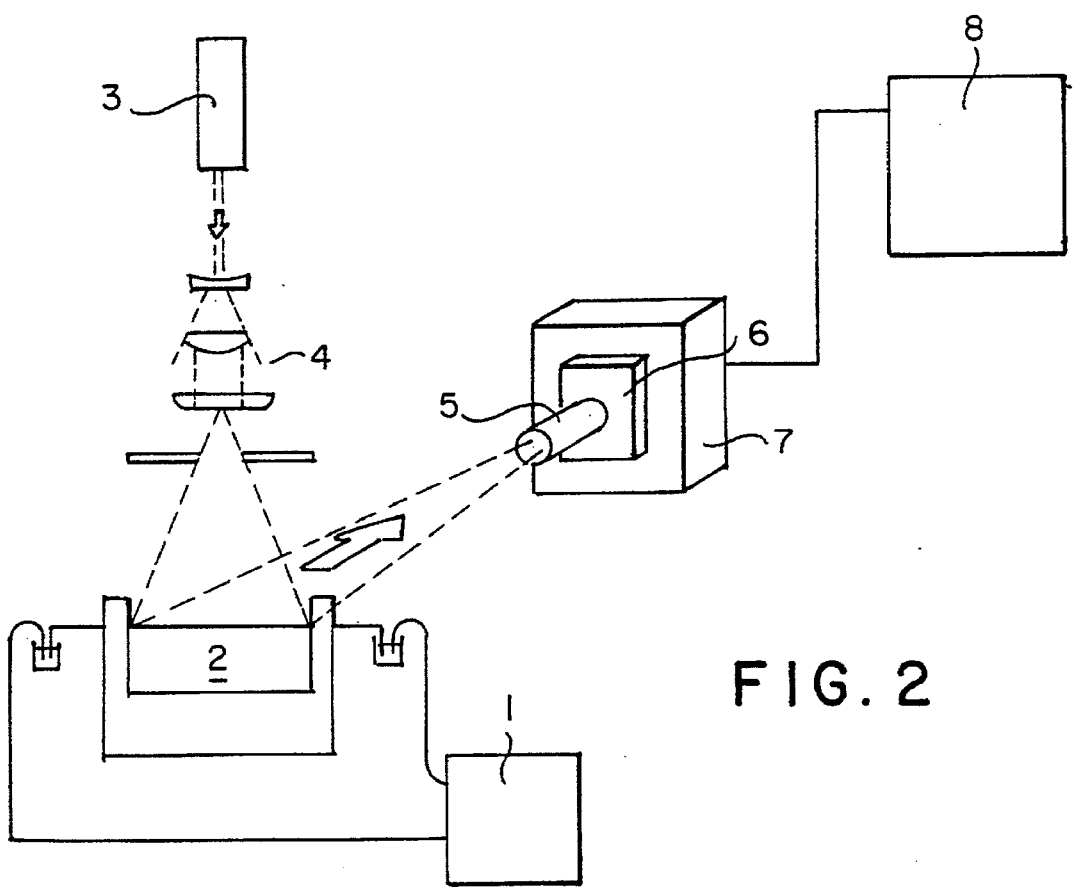
FIG. 2. Experimental set-up for separation and analysis of spectral properties of sample components using a cooled CCD camera as a detector.

passes via a lens system (5) and a light amplifier (6) into a CCD camera (7) with a cooled detector unit. The signal from the CCD camera is sent to a computer (8) provided with an image processing program. The display screen of the computer shows the separation process in the capillary (2) in real-time.

The invention is, of course, not restricted to the embodiments described above and shown in the drawings, but many modifications and changes may be made without departing from the general inventive concept as defined in the subsequent claims.

Figure 3:
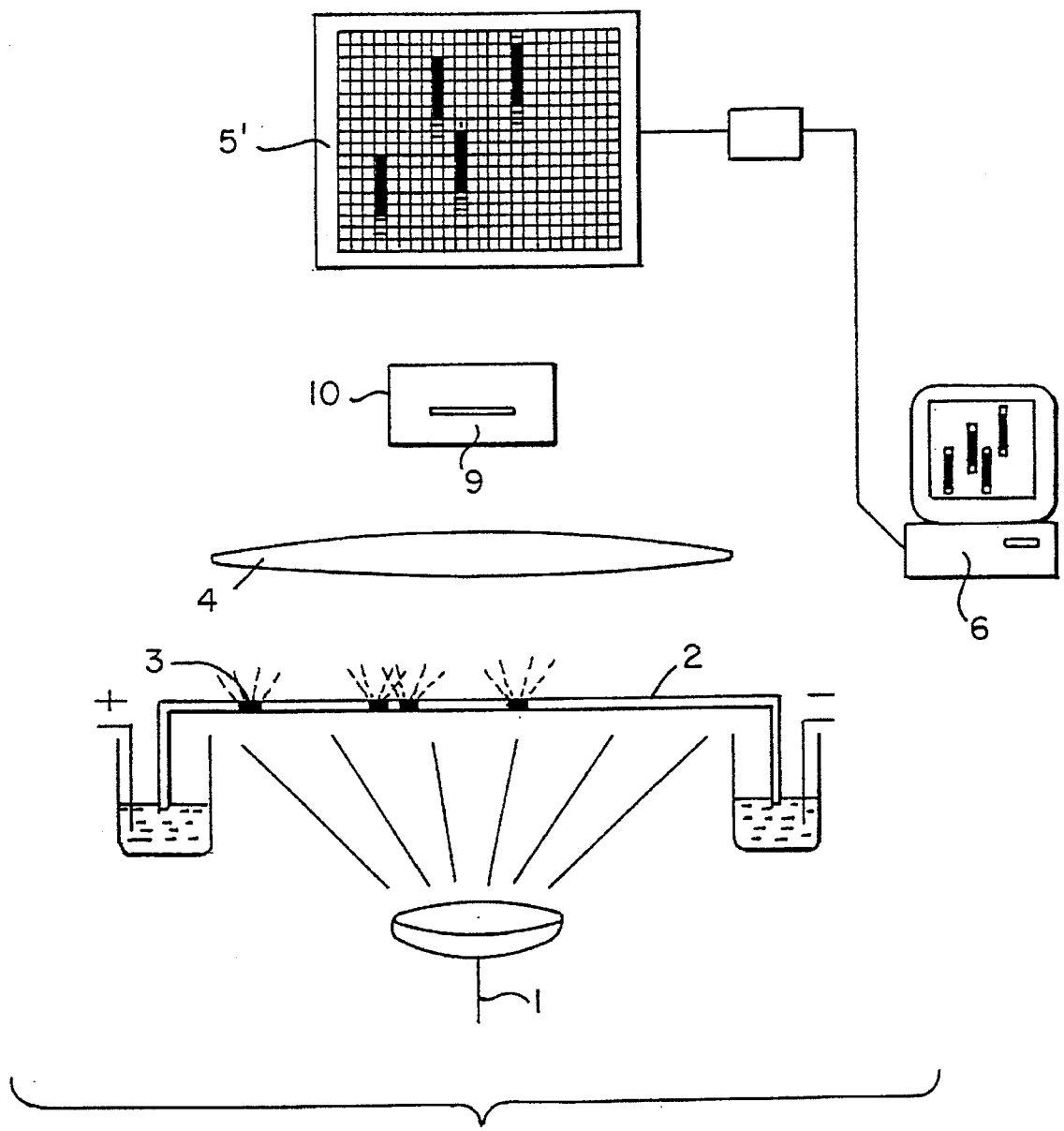
FIG. 3. Experimental set-up for separation and analysis of spectral properties of sample components using a spectrometer.

FIG. 3 shows an experimental set-up with a tow-dimensional CCD detector. A laser-light source with associated optics (1) irradiates the capillary electrophoretic capillary (2). Substances (3) present in the capillary (7) will then fluoresce. The fluorescent light is focused by a lens system (4) on the entrance slit (9) of a spectrometer (10). The spectrally resolved light falls on a two-dimensional CCD-detector (5'). The signal from the CCD-detector is sent to the computer (6) provided with an image processing program. The display screen of the computer shows the separation process in real time together with the spectral properties of the sample components (3).

Figure 4:
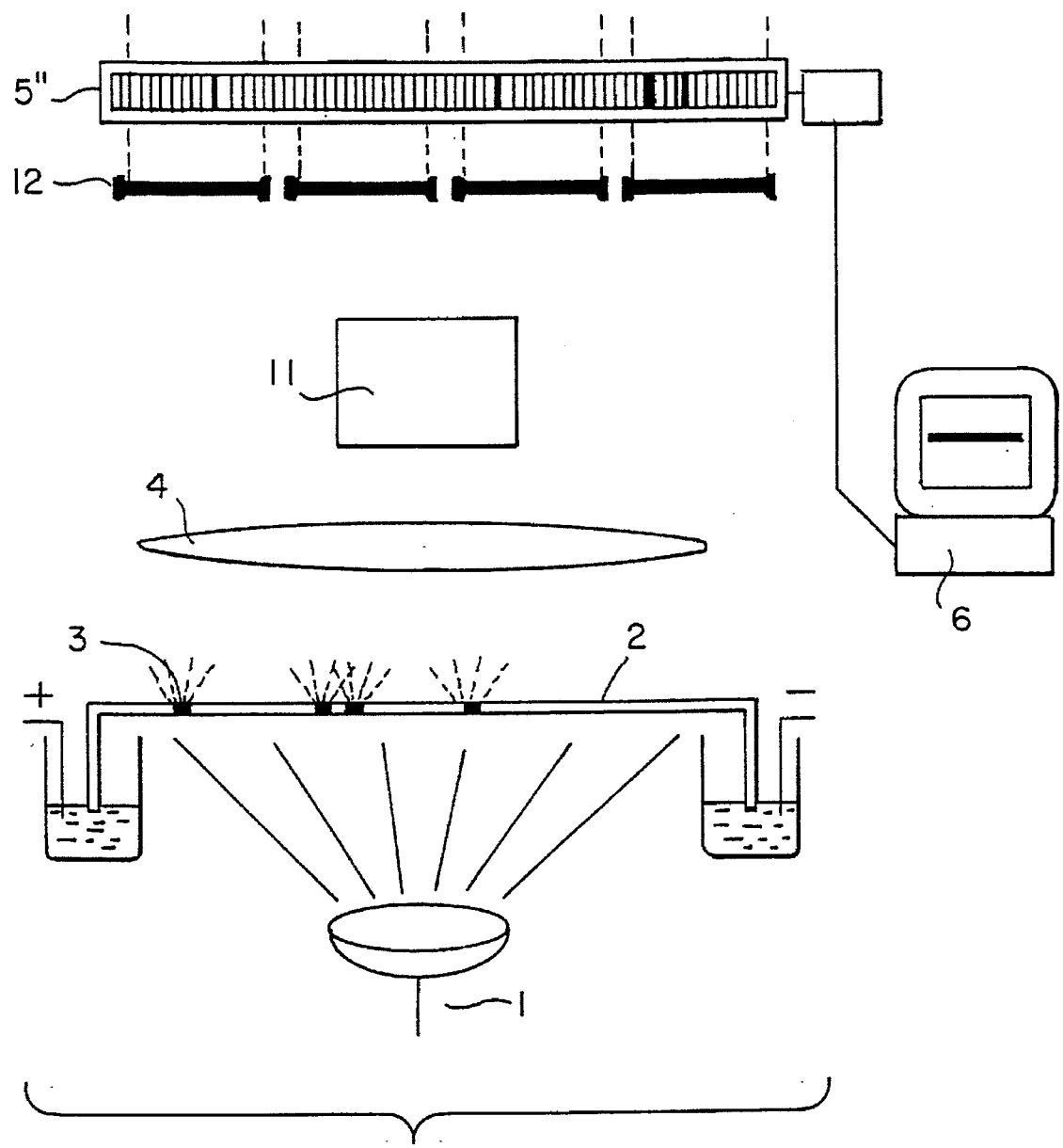
FIG. 4. Experimental set-up for separation and analysis of spectral properties of sample components using filter means for spectral filtration of optically divided emitted light.

FIG. 4 shows an experimental set-up with a diode row as a detector. A laser-light source with associated optics (1) irradiates the capillary electrophoretic capillary (2). Substances (3) present in the capillary (2) will then fluoresce. The fluorescent light is focused by a lens system (4), after which the fluorescent light is split into several beams by a mirror system (11) and imaged on a diode row detector (5") in adjacent sections. The beams are individually spectrally filtered by filters (12), each filter having unique transmission properties. The signal from the diode row detector is sent to the computer (6) provided with an image processing program. The display screen of the computer shows the separation process in real time together with the spectral properties as determined by the filters.

We claim:

1. A method of analyzing a sample by separating components of said sample in a thin capillary, irradiating said capillary, and detecting light selected from the group consisting of light emitted by and light absorbed by said components of said sample, comprising detecting said light at short intervals during said separating simultaneously over the whole or at least a large part of said capillary to create successive momentary images of the separation pattern and thereby the progress of the separation, thereby permitting termination of said separating when a desired separation of said components of said sample is achieved.

2. The method according to claim 1, wherein said detecting is based on fluorescence of said sample components.

3. The method according to claim 1, wherein said detecting is based on light scattering of said sample components.

4. The method according to claim 1, wherein said irradiating is performed using a laser.

5. The method according to claim 1, wherein said separating is carried out by capillary electrophoresis.

6. The method according to claim 1, 2, 3 or 4, wherein said separating is carried out by capillary column chromatography.

7. The method according to claim 1, wherein said separating is carried out by electrokinetic capillary chromatography.

8. The method of claim 1, wherein the termination of said separating occurs prior to complete migration of the sample components through said capillary.

9. The method of claim 1, wherein said irradiating and detecting occur over substantially the entire length of said capillary.

10. The method of claim 1, wherein said irradiating and detecting occur over a majority of the entire length of said capillary.

11. An apparatus for sample analysis by monitoring the pattern of separation of sample components and thereby the progress of separation thereof, comprising a separation capillary, a light source for irradiating said separation capillary, and a detector for detecting light selected from the group consisting of light emitted from and light emitted by said sample components, wherein said light source irradiates the whole or at least a large part of said separation capillary, and wherein said detector is an imaging detector arranged to register data at short intervals during the separation light emitted from or absorbed by said sample components depending on their spectral characteristics simultaneously over the whole or at least a large part of said separation capillary to create successive momentary images of said separation pattern and thereby the progress of said separation.

12. The apparatus according to claim 11, wherein the imaging detector is a two-dimensional charge coupled device.

13. The apparatus according to claim 12, wherein the charge coupled device detector is preceded by a spectrometer having an entrance slit onto which said separation capillary containing spatially resolved sample components is imaged for spectral resolution of light emitted from said sample components perpendicularly to said entrance slit, such that a spatial resolution is obtained in one direction of the two-dimensional detector and a spectral resolution is obtained in the other direction thereof.

14. The apparatus according to claim 11, wherein said imaging detector is a diode row.

15. The apparatus according to claim 14, wherein said diode row is preceded by (i) a beam division system arranged to optically divide said light emitted from said sample components into at least two beam paths and to individually focus said beam paths to image lines placed after one another on said diode row, and (ii) filter means for individual spectral filtration of said beam paths of emitted light.

16. The apparatus according to claim 15, wherein said light emitted from said sample components by said beam division system is optically divided into four beam paths.

17. The apparatus according to any one of claims 11 to 15, which further comprises a computer unit arranged to co-process registered data from said imaging detector for characterizing each of said sample components with regard to its spectral characteristics and classification by comparison with spectral information stored in said computer.

18. The apparatus of any one of claims 11–15 which further comprises a visual output means for displaying registered data.

19. The apparatus according to claim 11, wherein said separation capillary is selected from the group consisting of a capillary electrophoresis capillary, an electrokinetic chromatography capillary, and a capillary for capillary column chromatography.

20. The apparatus of claim 11, wherein said imaging detector is more than one diode row.

* * * * *